US012569674B2

(12) United States Patent
Chun et al.

(10) Patent No.: US 12,569,674 B2
(45) Date of Patent: Mar. 10, 2026

(54) ELECTRICAL STIMULATION SYSTEM

(71) Applicant: Korea University Research and Business Foundation, Seongbuk-Gu (KR)

(72) Inventors: Hoon Jai Chun, Seongbuk-gu (KR); Seung Han Kim, Seongbuk-gu (KR); Bo Ra Keum, Yongsan-gu (KR); Hyuk Soon Choi, Gangnam-gu (KR); Eun Sun Kim, Gangnam-gu (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 354 days.

(21) Appl. No.: 18/022,487

(22) PCT Filed: Jul. 16, 2021

(86) PCT No.: PCT/KR2021/009160
§ 371 (c)(1),
(2) Date: Feb. 21, 2023

(87) PCT Pub. No.: WO2022/039391
PCT Pub. Date: Feb. 24, 2022

(65) Prior Publication Data
US 2023/0256237 A1     Aug. 17, 2023

(30) Foreign Application Priority Data
Aug. 21, 2020    (KR) ........................ 10-2020-0105203

(51) Int. Cl.
| A61N 1/05 | (2006.01) |
| A61M 25/00 | (2006.01) |
| A61N 1/36 | (2006.01) |

(52) U.S. Cl.
CPC ... *A61N 1/0517* (2013.01); *A61M 2025/0095* (2013.01); *A61N 1/36007* (2013.01)

(58) Field of Classification Search
None
See application file for complete search history.

(56) References Cited

U.S. PATENT DOCUMENTS 3,754,555 A * 8/1973 Schmitt ................ A61N 1/0573
                                                    607/128
5,454,782 A     10/1995 Perkins
(Continued)

FOREIGN PATENT DOCUMENTS

| CN | 103796713 A | 5/2014 |
| JP | 2015-188483 A | 11/2015 |

(Continued)

*Primary Examiner* — Michael W Kahelin
(74) *Attorney, Agent, or Firm* — Christopher L. Johnson

(57) ABSTRACT

An electrical stimulation system according to an embodiment may comprise: a catheter having a long and thin tubular shape; an electrode disposed at one end of the catheter and inserted into a target portion; an electrical stimulator for generating electrical stimulation to be applied onto the target portion by the electrode; and a control part for controlling an electrical pulse of the electrical stimulator to change the electrical stimulation applied onto the target portion, wherein the electrode applies electrical stimulation in a state where a distal end of the electrode is enlarged and fixed to a target portion.

14 Claims, 4 Drawing Sheets

(56)                    References Cited

U.S. PATENT DOCUMENTS

| | | | |
|---|---|---|---|
| 6,106,521 | A | 8/2000 | Blewett et al. |
| 6,615,084 | B1 | 9/2003 | Cigaina |
| 7,835,801 | B1 * | 11/2010 | Sundararajan ....... A61N 1/0573 |
| | | | 607/119 |
| 9,561,369 | B2 | 2/2017 | Burnes et al. |
| 9,925,367 | B2 | 3/2018 | Sharma et al. |
| 2006/0015162 | A1 * | 1/2006 | Edward .................... A61N 1/06 |
| | | | 606/41 |
| 2008/0132982 | A1 | 6/2008 | Gerber |
| 2009/0076409 | A1 | 3/2009 | Wu et al. |
| 2009/0276025 | A1 * | 11/2009 | Burnes ............... A61N 1/36085 |
| | | | 607/116 |
| 2012/0323175 | A1 * | 12/2012 | Vogelbaum ....... A61M 25/0102 |
| | | | 604/95.04 |
| 2015/0005762 | A1 | 1/2015 | Belk et al. |
| 2016/0015451 | A1 | 1/2016 | Shikhman |
| 2020/0038096 | A1 * | 2/2020 | Schepis ................. A61B 5/296 |

FOREIGN PATENT DOCUMENTS

| | | |
|---|---|---|
| JP | 2016-501641 A | 1/2016 |
| JP | 6108410 | 3/2017 |
| KR | 10-2007-0035155 | 3/2007 |

* cited by examiner

ELECTRICAL STIMULATION SYSTEM

TECHNICAL FIELD

Disclosed is an electrical stimulation system.

Disclosed is, more particularly, an electrical stimulation system for treating reflux esophagitis by controlling an esophageal motion by directly applying electrical pulse stimulation to the lower esophageal sphincter.

BACKGROUND ART

Gastroesophageal reflux disease (GERD) is a condition affecting 14-17% of the population in the United States and Western Europe. The total annual cost of treatment for GERD in the United States is estimated to be approximately $9.8 billion, of which $5.8 billion is spent on medication. More than one-third of GERD patients continue to have weak acid or non-acid reflux, and GERD symptoms persist despite high-dose acid suppression therapy with proton pump inhibitors (PPIs). In addition, there are growing concerns about the long-term safety of PPIs, leading patients and doctors to choose alternative treatment options. Also, new drugs such as P-CAB have recently been developed and used, but there is not enough information on long-term efficacy and safety.

Currently, drugs, endoscopic procedures, and surgical operations are performed for the treatment of GERD, but they are not effective, the burden of the procedure is high for the patient, and there are many complications. In addition, less than 1% of the subjects who are indicated for the risk and complications of the surgical operation undergo reflux prevention surgery. In recent years, concerns about the safety and long-term efficacy of reflux prevention surgery have led to a steady decline in the number of reflux prevention surgeries worldwide.

Clinically, drugs and behavioral therapies for the treatment of functional esophageal motility disorders such as GERD are implemented, but new treatments are urgently needed because the effects thereof are not significant. To overcome this, there are increasing interest and demand for an electric stimulation technology for lower esophageal sphincter (a gastric electrical stimulator; GES).

The above description is information the inventor(s) acquired during the course of conceiving the present disclosure, or already possessed at the time, and was not necessarily publicly known before the present application was filed.

Prior Document: Korean Laid-open Patent Publication No. 10-2007-0035155 (Published on Mar. 30, 2007)

DISCLOSURE OF THE INVENTION

Technical Goals

An object according to an embodiment is to provide an electrical stimulation system capable of being inserted to an endoscope for stomach and applying accurate electrical stimulation onto a desired target portion in a non-invasive manner.

The technical goals of the embodiments are not limited to what is described in the foregoing, and other technical goals that are not mentioned above may also be clearly understood by those skilled in the art from the following description.

Technical Solutions

An electrical stimulation system according to an embodiment for achieving the above object includes a catheter having a long and thin tubular shape, an electrode disposed at one end of the catheter and inserted into a target portion, an electrical stimulator for generating electrical stimulation to be applied onto the target portion by the electrode, and a control part for controlling an electrical pulse of the electrical stimulator to change the electrical stimulation applied onto the target portion.

According to an aspect, the electrode may include a plurality of through holes penetrating from inside of the distal end of the electrode to an outer side surface, and a plurality of fixing members provided to be movable inside the through hole, and each of the plurality of fixing members may be enlarged to protrude outside of the distal end of the electrode so that the distal end of the electrode is fixedly inserted into the target portion.

According to an aspect, the through hole may extend obliquely from the inside of the distal end of the electrode toward the outer side surface, and each of the fixing members may move along the through hole to protrude outside of the electrode or return to inside of the electrode.

According to an aspect, the through hole may extend in a radial direction from the inside of the distal end of the electrode toward the outer side surface, and each of fixing members may have an end portion formed in an L-shape to extend to protrude outside of the electrode or to return to the inside of the electrode through the through According to an aspect, the control part may control an operation of the fixing member to fix the electrode to the target portion or release the fixation.

According to an aspect, the catheter may be placed toward the target portion by using an endoscope.

According to an aspect, a material of the electrode may be copper, platinum, silver, or stainless steel.

According to an aspect, the electrical stimulator may further include a wire disposed inside the catheter and extending in a longitudinal direction of the catheter, and the wire has one end connected to the electrode and the other end connected to the electrical stimulator to deliver electrical stimulation generated from the electrical stimulator to the electrode.

An electric stimulus apparatus according to an example for achieving the above object includes a catheter having a long and thin tubular shape, an electrode disposed at one end of the catheter and inserted into a target portion, and an electrical stimulator for generating electrical stimulation to be applied onto the target portion by the electrode, and the electrode applies electrical stimulation in a state where a distal end of the electrode is enlarged and fixed to a target portion.

According to an aspect, the electrode may include a plurality of through holes penetrating from inside of the distal end of the electrode to an outer side surface, and a plurality of fixing members provided to be movable inside the through hole, and each of the plurality of fixing members may be enlarged to protrude outside of the distal end of the electrode so that the distal end of the electrode is fixedly inserted into the target portion.

According to an aspect, the through hole may extend obliquely from the inside of the distal end of the electrode toward the outer side surface, and each of the fixing members may move along the through hole to protrude outside of the electrode or return to inside of the electrode.

According to an aspect, the through hole may extend in a radial direction from the inside of the distal end of the electrode toward the outer side surface, and each of the fixing members may have an end portion formed in an L-shape to extend to protrude outside of the electrode or to return to the inside of the electrode through the through Effects According to the electrical stimulation system according to an embodiment, the effects of inserting the electrical stimulation system to the endoscope for stomach and applying accurate electrical stimulation onto a desired target portion in a non-invasive manner may be exhibited.

The effects of the electrical stimulation system according to an embodiment are not limited to the above-mentioned effects, and other effects that are not mentioned above may also be clearly understood by those skilled in the art from the following description.

Figure 1:
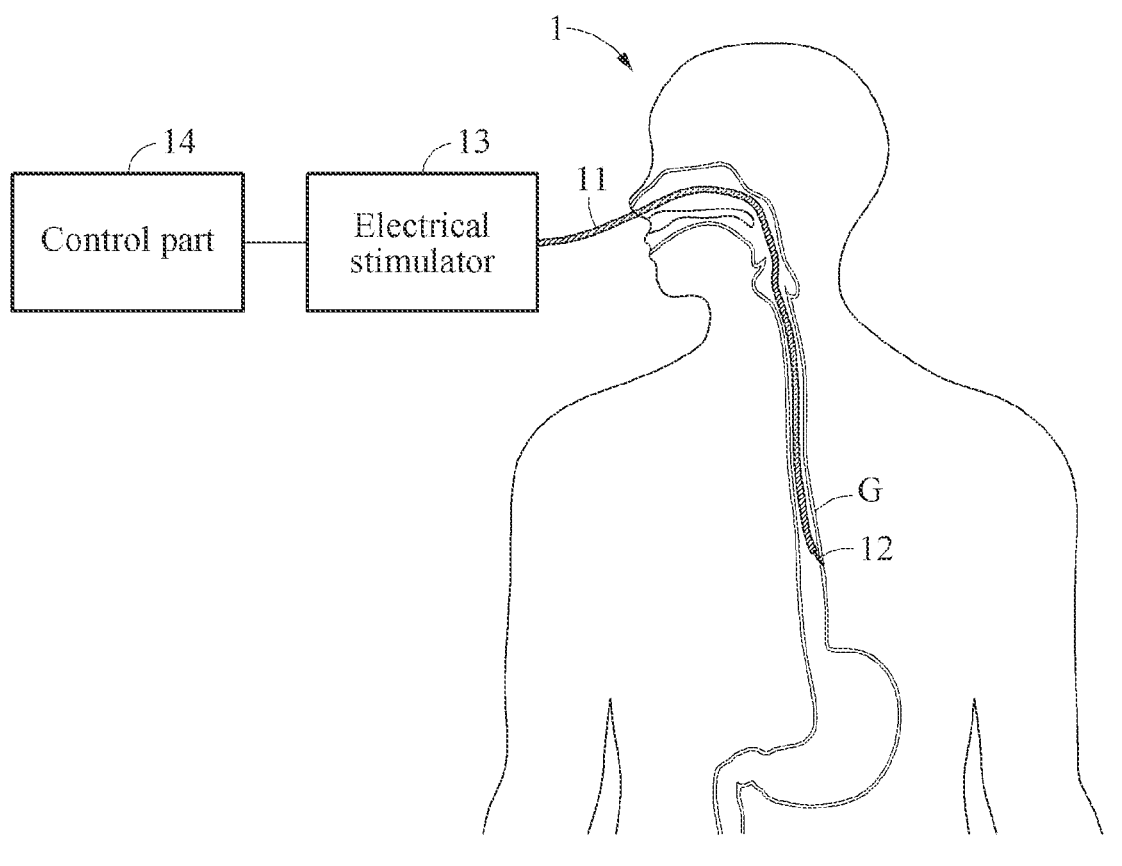
FIG. 1 is a diagram schematically illustrating a structure of an electrical stimulation system according to an embodiment.

The accompanying drawings illustrate preferred example embodiments of the present disclosure, and are provided together with the detailed description for better understanding of the technical idea of the present disclosure. Therefore, the present disclosure should not be construed as being limited to the example embodiments set forth in the drawings.

BEST MODE FOR CARRYING OUT THE INVENTION

Hereinafter, embodiments will be described in detail with reference to the accompanying drawings. However, various alterations and modifications may be made to the embodiments. Here, the embodiments are not construed as limited to the disclosure. The embodiments should be understood to include all changes, equivalents, and replacements within the idea and the technical scope of the disclosure.

The terminology used herein is for the purpose of describing particular embodiments only and is not to be limiting of the embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the embodiments with reference to the accompanying drawings, like reference numerals refer to like components and a repeated description related thereto will be omitted. In the description of example embodiments, detailed description of well-known related structures or functions will be omitted when it is deemed that such description will cause ambiguous interpretation of the present disclosure.

In addition, terms such as first, second, A, B, (a), (b), and the like may be used to describe components of the embodiments. These terms are used only for the purpose of discriminating one component from another component, and the nature, the sequences, or the orders of the components are not limited by the terms. It should be noted that if one component is described as being "connected," "coupled" or "joined" to another component, the former may be directly "connected," "coupled," and "joined" to the latter or "connected", "coupled", and "joined" to the latter via another component.

The same name may be used to describe an element included in the example embodiments described above and an element having a common function. Unless stated otherwise, the description of an embodiment may be applicable to other embodiments, and a repeated description related thereto is omitted.

FIG. 1 is a diagram schematically illustrating a structure of an electrical stimulation system 1 according to an embodiment.

Figure 2:
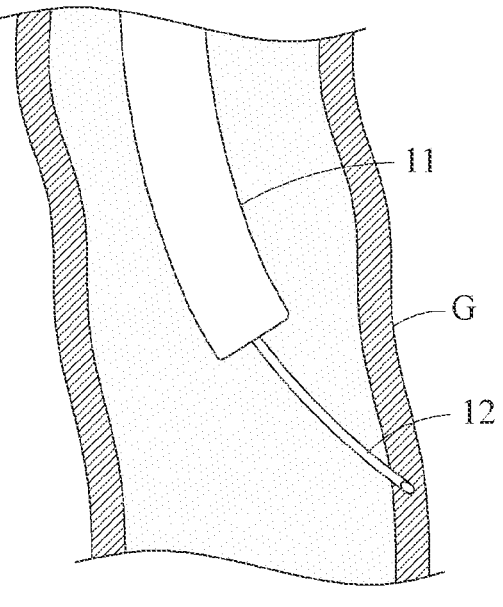
FIG. 2 is a diagram illustrating that an electrode of an electrical stimulation system is in contact with a target portion according to an embodiment.

FIG. 2 is a diagram illustrating that an electrode 12 of the electrical stimulation system 1 according to an embodiment is in contact with a target portion G.

Referring to FIGS. 1 and 2, the electrical stimulation system 1 according to an embodiment may be inserted into the body through the nasal cavity and apply electrical stimulation onto the target portion in a non-invasive manner. Here, the target portion G may be the lower esophagus.

For example, the electrical stimulation system 1 may include a catheter 11, an electrode 12, an electrical stimulator 13, and a control part 14.

Specifically, the catheter 11 may be inserted into the body through the nasal cavity and may reach the target portion G by moving along the esophagus. For example, the catheter 11 may be inserted using an endoscope and placed on the target portion G. This catheter 11 may be provided in a long and thin tubular shape.

The electrode 12 is disposed at one end of the catheter 11 and moves to the target portion G as the catheter moves along the esophagus, and an end portion of the electrode may be positioned at the target portion G, that is, the lower esophagus. The electrode 12 may be inserted and fixed to the gastric mucosa (GM) of the lower esophagus to apply electrical stimulation. A material of the electrode 12 may be, for example, copper, platinum, silver, or stainless steel. In addition, the electrode 12 may have a thickness and length suitable for applying the electrical stimulation onto the target portion G.

At this time, the electrode 12 may be fixedly inserted into the target portion G in a state where a distal end thereof is enlarged to stably deliver the electrical stimulation to the target portion G. Details thereof will be described in detail with reference to FIGS. 3 to 8.

The electrical stimulator 13 may be positioned outside the body and generate the electrical stimulation to be applied onto the target portion G by the electrode 12.

At this time, the electrical stimulator 13 may be electrically connected to the electrode 12 through a wire (not shown).

The wire may be disposed inside the catheter 11 and may be formed in a structure to extend in a longitudinal direction of the catheter 11. One end of the wire may be connected to the electrode 12 and the other end of the wire may be connected to the electrical stimulator 13. Accordingly, the electrical stimulation generated from the electrical stimulator 13 positioned outside the body may be transferred to the electrode 12 inserted into the target portion G so that electrical stimulation may be applied onto the target portion G.

The control part 14 may be configured to control the electrode 12 and the electrical stimulator 13. For example, in order to fix the electrode 12 to the target portion G, the control part 14 may control the electrode 12 so that a distal end portion of the electrode 12 inserted into the target portion G is enlarged. In addition, the control part 14 may control a pulse of the electrical stimulation generated from the electrical stimulator 13 so as to change the electrical stimulation to be applied onto the target portion G.

Hereinafter, the components of the electrode 12 will be described in detail with reference to FIGS. 3 and 4.

Figure 3:
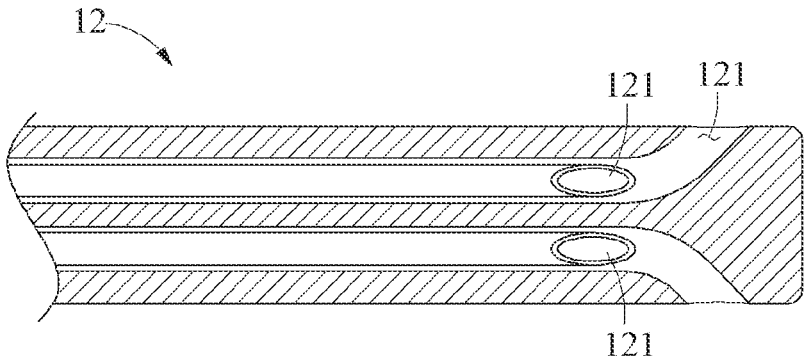
FIG. 3 is a diagram illustrating fixing members provided on a distal end of an electrode of an electrical stimulation system according to an embodiment.

FIG. 3 is a diagram illustrating fixing members 121 provided on a distal end of the electrode 12 of the electrical stimulation system 1 according to an embodiment.

Figure 4:
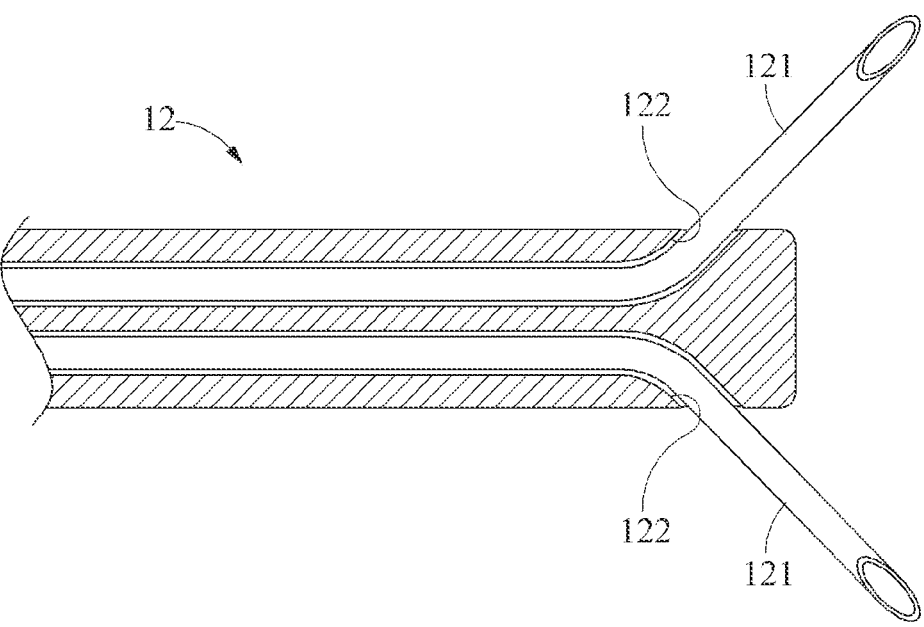
FIG. 4 is a diagram illustrating that fixing members provided on a distal end of an electrode of an electrical stimulation system are enlarged according to an embodiment.

FIG. 4 is a diagram illustrating that the fixing members 121 provided on the distal end of the electrode 12 of the electrical stimulation system 1 are enlarged according to an embodiment.

Referring to FIGS. 3 and 4, the electrode 12 may include the fixing member 121 and through hole 122.

Each of the through holes 122 may be formed to penetrate the inside of the distal end of the electrode 12 along a longitudinal direction of the electrode 12. For example, the through hole 122 may penetrate from the inside of the electrode 12 to an outer surface of the electrode 12. At this time, the through hole 122 may extend obliquely toward the outer side surface. The through hole 122 may be provided in plurality and these may be provided as individual passages, respectively, to form openings at different positions on the outer surface from the inside of the electrode 12.

The fixing member 121 may be provided in plurality and these may be disposed inside the different through holes 122, respectively. The fixing members 121 may be provided to protrude to the outside of the electrode 12 through the openings from the inside of the through holes 122 or to be movable from the outside of the electrode 12 to the inside of the through holes 122.

For example, the fixing member 121 may have an elongated shape. In addition, as shown in FIG. 4, when the fixing member 121 moves in the longitudinal direction toward the outside of the electrode 12, an end portion thereof may be deployed in a bent shape along the through hole 122 extending obliquely.

The end portion of the fixing member 121 deployed as described above may protrude to the outside of the electrode 12 so as to enlarge the distal end portion of the electrode 12. Accordingly, the protruding end portion of the fixing member 121 may be inserted into the target portion G.

In addition, the end portion of the fixing member 121 may be formed in a shape of an anchor. As the electrode is fixed to the target portion G by such a shape, the electrode 12 may be prevented from being separated from the position where it is inserted into the target portion G. That is, the electrode 12 may be fixed while being inserted into the target portion G by the fixing member 121.

On the other hand, each of the fixing members 121 shown in FIG. 4 may retract obliquely along the through hole 122 so as to return to the inside of the electrode 12, as shown in FIG. 3, from the outside of the electrode 12. Accordingly, the fixation of the electrode 12 to the target portion G may be released.

Hereinafter, an electrode 22 including fixing members 221 having a different shape will be described in detail with reference to FIGS. 5 and 6.

Figure 5:
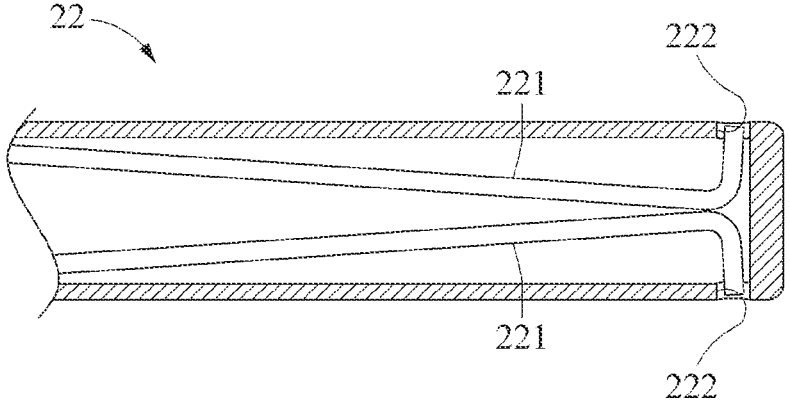
FIG. 5 is a diagram illustrating fixing members provided on a distal end of an electrode of an electrical stimulation system according to another embodiment.

FIG. 5 is a diagram illustrating the fixing members 221 provided on a distal end of the electrode 22 of an electrical stimulation system 2 according to another embodiment.

Figure 6:
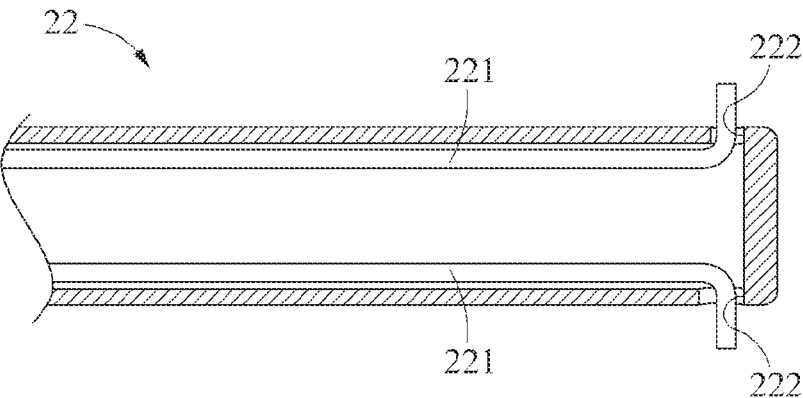
FIG. 6 is a diagram illustrating that fixing members provided on a distal end of an electrode of an electrical stimulation system are enlarged according to another embodiment.

FIG. 6 is a diagram illustrating that the fixing members 221 provided on the distal end of the electrode 22 of the electrical stimulation system 2 are enlarged according to another embodiment.

Referring to FIGS. 5 and 6, the electrode 22 may include the fixing members 221 and through holes 222.

The electrode 22 of the electrical stimulation system 2 according to another embodiment may have a hollow shape.

The through hole 222 may be formed to extend from a distal end portion of the electrode 22 in a direction perpendicular to a central axis of the electrode 22, that is, in a radial direction. For example, the through hole 222 may be formed to penetrate an outer surface of the electrode 22 from a hollow inside the electrode 22 so that the inside and outside of the electrode 22 communicate with each other.

The through hole 222 may be provided in plurality and these may be provided as individual passages, respectively, to form openings at different positions on the outer surface from the inside of the electrode 22.

The fixing member 221 may be provided in plurality and disposed inside the electrode 22. The fixing member 221 may be provided so that an end portion thereof protrudes to the outside of the electrode 22 through the through hole 222 or is movable from the outside to the inside of the electrode 22 again.

For example, the fixing member 221 may have an elongated body. In addition, one end of the fixing member 221 may be provided in an L-shape so as to be orthogonal to the body.

The fixing member 221 described above may protrude to the outside of the electrode 22 in the radial direction through the through hole 222.

Additionally, the other end of each of the fixing members 221 may be rotatably fixed to the same point provided inside the electrode 22.

Accordingly, the plurality of fixing members 221 are deployed so that the end portions having the L-shape are spread apart, and thus the fixing members may protrude to the outside of the electrode 22 through the through hole 222 or retract in the opposite direction to return to the inside of the electrode 22 from the outside of the electrode 22 again.

The end portion of the fixing member 221 operating in this way may protrude outside the electrode 22 to enlarge the distal end portion of the electrode 22. Therefore, the protruding end portion of the fixing member 221 may be inserted into the target portion G.

In addition, the end portion of the fixing member 221 may be formed in a shape of an anchor. As the electrode is fixed to the target portion G by such a shape, the electrode 22 may be prevented from being separated from the position where it is inserted into the target portion G. That is, the electrode 22 may be fixed while being inserted into the target portion G by the fixing member 221.

On the other hand, each of the fixing members 221 may return to the inside of the electrode 22 by retracting toward the inside of the electrode 22. Accordingly, the fixation of the electrode 22 to the target portion G may be released.

Figure 7:
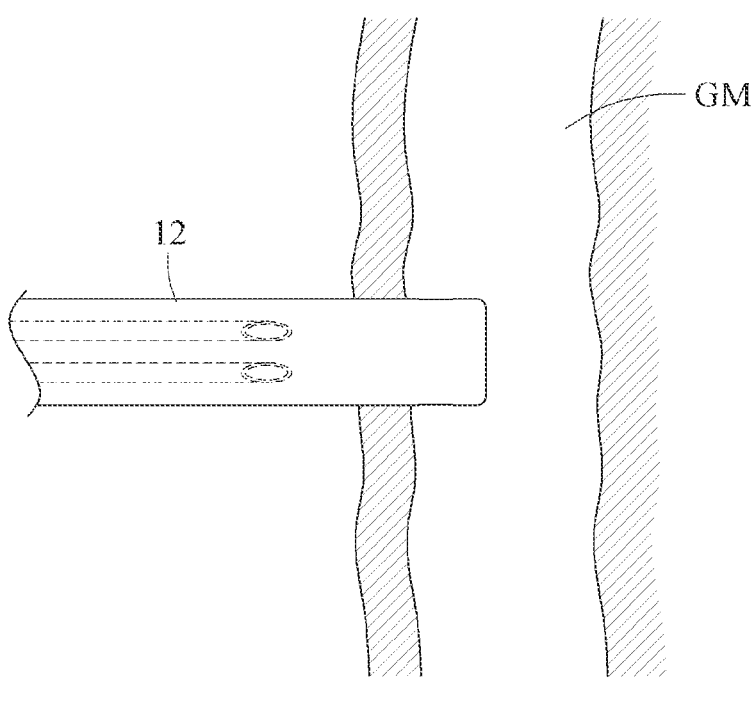
FIG. 7 is a diagram illustrating that the electrode of FIG. 4 is inserted to a target portion.

FIG. 7 is a diagram illustrating that the electrode 12 of FIG. 4 is inserted into the target portion G.

Figure 8:
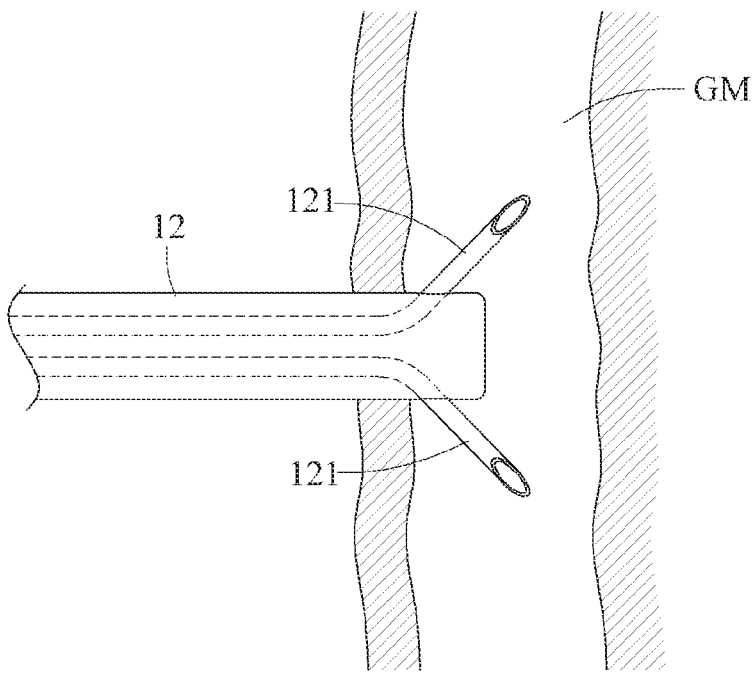
FIG. 8 is a diagram illustrating that the electrode of FIG. 7 is fixed by the fixing members.

FIG. 8 is a diagram illustrating that the electrode 12 of FIG. 7 is fixed by the fixing members 121.

Referring to FIG. 7, the electrode 12 may be inserted into the gastric mucosa (GM) of the lower esophagus.

Then, as shown in FIG. 8, the fixing members 121 at the distal end of the electrode 12 may be deployed in the target portion G. Therefore, the electrode 12 may remain inserted into the target portion G as long as the fixing members 121 are deployed.

Although not shown, similarly to the case of the fixing members 221 of FIG. 6, when the electrode 22 is inserted into the GM, the fixing member 221 may be deployed so that the electrode 22 is fixed while being inserted thereto.

Also, the operation of the fixing member 121 may be controlled by the control part 14.

In a case of the fixing member 121 shown in FIGS. 3 and 4, the control part 14 may push or pull an end portion of the fixing member 121 closer to the control part 14.

Specifically, the fixing member 121 may be moved toward the outside of the electrode 12 by the pushing force of the control part 14. Conversely, the fixing member 121 may be moved toward the inside of the electrode 12 by the pulling force of the control part 14.

Similar to the foregoing, in a case of the fixing member 221 shown in FIGS. 5 and 6, the control part 14 may control a deployment direction of the fixing member 221.

Specifically, the control part 14 may control the end portion of each fixing member 221 to be deployed in the radial direction toward the outside of the electrode 22. Accordingly, the end portion of the fixing member 221 may protrude outside the electrode 22 through the through hole 222. Conversely, the control part 14 may control the end portion of each fixing member 221 to be deployed in the radial direction toward the inside of the electrode 22. Accordingly, the end portion of the fixing member 221 may return to the inside from the outside of the electrode 22 through the through hole 222.

As described above, the control part 14 may control the operation of the fixing members 121 and 221 to fix the electrodes 12 and 22 to the target portion G or to release the fixation.

Also, the control part 14 may control electrical stimulation generated by the electrical stimulator 13. For example, the control part 14 may control a potential of the electrical stimulation. In addition, the control part 14 may control an electrical pulse of the electrical stimulator 13 to realize various forms of current flows. Further, the control part 14 may also set a duty cycle, frequency, current, and the like of an electrical signal variously to realize various forms of current flows in the target portion G to which the electrical stimulation is applied.

The electrical stimulation system 1 according to an embodiment may also be implemented as an electrical stimulation device.

Such an electrical stimulation device may be used for patients described below.

1. Patients with refractory gastroesophageal reflux disease (patients with gastroesophageal reflux disease who do not respond to conventional drug treatment for 2-3 months)

2. Patients with high risk or complications such as esophageal stricture caused by gastroesophageal reflux disease 3. Patients who have responded to conventional treatment, but whose quality of life has deteriorated due to symptoms such as chest pain and reflux symptoms 4. Patients who are concerned or concern about drug side effects while they need to get drug administration for a long period of time due to gastroesophageal reflux disease In order to treat the above-mentioned targets, regarding the electrical stimulation device, a disposable endoscope catheter 11 and an electrode 12 disposed at one end of the catheter 11 may be inserted through a gastroscopic channel during conscious sedation endoscopy of a patient. After a distal end portion of the electrode 12 is fixed to a muscular layer of the esophagus, the endoscope is retrieved, and the catheter 11 may be fixed through the nasal cavity. The electrical stimulation device fixed in this way may perform an electrical stimulation treatment while remaining placed for about 7 to 30 days in consideration of the patient's condition.

While the example embodiments are described with reference to drawings, it will be apparent to one of ordinary skill in the art that various alterations and modifications in form and details may be made in these example embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents.

Therefore, other implementations, other embodiments, and equivalents to the claims are also within the scope of the following claims.

The invention claimed is:

1. An electric stimulation system comprising:
a catheter having a long and thin tubular shape;
an electrode disposed at one end of the catheter and configured to be inserted into a target portion;
a plurality of through holes penetrating from inside of a distal end of the electrode to an outer side surface of the electrode, the plurality of through holes each comprising a respective passageway extending along a longitudinal axis of the electrode;
an electrical stimulator for generating electrical stimulation to be applied onto the target portion by the electrode; and
a controller configured to control an electrical pulse of the electrical stimulator to change the electrical stimulation applied onto the target portion,
wherein the electrode applies electrical stimulation in a state where a distal end of the electrode is enlarged and fixed to a target portion.

2. The electric stimulation system of claim 1,
wherein the electrode comprises:

a plurality of fixing members provided to be movable inside a respective through hole of the plurality of through holes, and wherein each of the plurality of fixing members are configured to be enlarged to protrude outside of the distal end of the electrode so that, during use, the distal end of the electrode is fixedly inserted into the target portion.

3. The electric stimulation system of claim 2, wherein the plurality of through holes each extend obliquely from the inside of the distal end of the electrode toward the outer side surface, and wherein each of the fixing members moves along a respective through hole of the plurality of through holes to protrude outside of the electrode or return to inside of the electrode.

4. The electric stimulation system of claim 2, wherein the plurality of through holes each extend in a radial direction from the inside of the distal end of the electrode toward the outer side surface, and wherein each of the fixing members has an end portion formed in an L-shape to extend to protrude outside of the electrode or to return to the inside of the electrode through a respective through hole of the plurality of through holes.

5. The electric stimulation system of claim 2, wherein electrode is operable to be releasably fixed to the target portion via the fixing member.

6. The electric stimulation system of claim 1, further comprising an endoscope, wherein the catheter is configured to be placed toward the target portion using the endoscope.

7. The electric stimulation system of claim 1, wherein a material of the electrode is copper, platinum, silver, or stainless steel.

8. The electric stimulation system of claim 1, further comprising:

a wire disposed inside the catheter and extending in a longitudinal direction of the catheter, wherein the wire has one end connected to the electrode and the other end connected to the electrical stimulator to deliver electrical stimulation generated from the electrical stimulator to the electrode.

9. An electric stimulation device comprising:

a catheter having a long and thin tubular shape;

an electrode disposed at one end of the catheter and configured to be inserted into a target portion;

a plurality of through holes penetrating from inside of a distal end of the electrode to an outer side surface of the electrode, the plurality of through holes each comprising a respective passageway extending along a longitudinal axis of the electrode; and an electrical stimulator for generating electrical stimulation to be applied onto the target portion by the electrode, wherein the electrode applies electrical stimulation in a state where a distal end of the electrode is enlarged and fixed to a target portion.

10. The electric stimulation device of claim 9, wherein the electrode comprises:

a plurality of through holes penetrating from inside of the distal end of the electrode to an outer side surface; and a plurality of fixing members provided to be movable inside a respective through hole of the plurality of through holes, and wherein each of the plurality of fixing members is enlarged and configured to protrude outside of the distal end of the electrode so that the distal end of the electrode, during use, is fixedly inserted into the target portion.

11. The electric stimulation device of claim 10, wherein the plurality of through holes each extend obliquely from the inside of the distal end of the electrode toward the outer side surface, and wherein each of the fixing members moves along a respective through hole of the plurality of through holes to protrude outside of the electrode or return to inside of the electrode.

12. The electric stimulation device of claim 10, wherein the plurality of through holes each extend in a radial direction from the inside of the distal end of the electrode toward the outer side surface, and wherein each of the fixing members has an end portion formed in an L-shape to extend to protrude outside of the electrode or to return to the inside of the electrode through a respective through hole of the plurality of through holes.

13. A method for electrically stimulating a target portion of a body of a human, the method comprising:

obtaining a catheter comprising an electrode disposed at one end of the catheter, the electrode comprising a plurality of through holes penetrating from inside of a distal end of the electrode to an outer side surface of the electrode, the plurality of through holes each comprising a respective passageway extending along a longitudinal axis of the electrode;

controlling the catheter to insert the electrode into the target region;

enlarging and fixing a distal end of the electrode to the target portion;

operating an electrical stimulator to generate an electrical stimulation to be applied onto the target portion by the electrode;

applying the electrical stimulation to the target portion; and controlling an electrical pulse of the electrical stimulator to change the electrical stimulation applied onto the target portion.

14. The method of claim 13, further comprising controlling an operation of a fixing member to fix the electrode to the target portion.

* * * * *